United States Patent [19]

Burke

[11] Patent Number: 5,145,995

[45] Date of Patent: * Sep. 8, 1992

[54] PROCESS FOR THE MANUFACTURE OF 3-PENTENOIC ACID

[75] Inventor: Patrick M. Burke, Wilmington, Del.

[73] Assignee: E. I. du Pont de Nemours and Company, Wilmington, Del.

[*] Notice: The portion of the term of this patent subsequent to Nov. 29, 2005 has been disclaimed.

[21] Appl. No.: 371,185

[22] Filed: Jun. 26, 1989

[51] Int. Cl.$^5$ .............................................. C07C 51/14
[52] U.S. Cl. ................................................... 562/522
[58] Field of Search ......................................... 562/522

[56] References Cited

U.S. PATENT DOCUMENTS 4,788,334  11/1988  Burke .................................. 562/522

Primary Examiner—Jose G. Dees
Assistant Examiner—B. Frazier
Attorney, Agent, or Firm—Earl L. Handley

[57] ABSTRACT

Preparation of 3-pentenoic acid from butadiene, water and carbon monoxide in an organic acid solvent in the presence of a rhodium catalyst and a bromide or iodide promoter.

20 Claims, No Drawings

PROCESS FOR THE MANUFACTURE OF 3-PENTENOIC ACID

FIELD OF THE INVENTION

This invention relates to an improved process for the manufacture of 3-pentenoic acid by the hydrocarboxylation of butadiene.

BACKGROUND OF THE INVENTION

Most of the methods described in the prior art for the reaction of olefins with carbon monoxide and water to form the corresponding carboxylic acids either require extreme reaction conditions or produce the desired acids in very low yield. Recently, however, it has been shown that bromide- or iodide-promoted rhodium compounds are effective catalysts for the hydrocarboxylation of olefins under relatively mild conditions.

In U.S. Pat. No. 3,579,552, Craddock et al. disclose a process for the preparation of carboxylic acids by the reaction of ethylenically unsaturated compounds with carbon monoxide and water, in the presence of catalyst compositions essentially comprising rhodium compounds and complexes, together with an iodide promoter.

In U.S. Pat. No. 4,690,912, Paulik et al. disclose a bromide- or iodide- promoted rhodium catalyst system for the carbonylation of carbonylatable reactants.

In U.S. Pat. No. 4,622,423, Burke discloses the preparation of 3-pentenoic acid by hydrocarboxylating butadiene with carbon monoxide and water in the presence of a rhodium-containing catalyst, an iodide promoter and certain halocarbon solvents. Methylene chloride is the preferred solvent; acetic acid in aqueous solution is said to be undesirable.

In U.S. Pat. No. 4,788,334, Burke discloses a process for the hydrocarboxylation of linear olefinically unsaturated esters and terminally unsaturated alkenes having 4 to 16 carbon atoms to form a mixture which contains an increased amount of the linear carboxylate acid. The reaction mixture comprises the ester or the terminally unsaturated alkene, carbon monoxide, water, a halocarbon or aromatic solvent, a rhodium catalyst, an iodide promoter and a mildly acidic accelerator.

Although the prior art does disclose the use of halide-promoted rhodium catalysts for the hydrocarboxylation of butadiene, there is still a need for a process in which butadiene can be hydrocarboxylated in high yields with high linear selectivity and at high rates. The object of this invention is to provide such a process for the preparation of 3-pentenoic acid, a potential precursor to the commercially important dicarboxylic acid, adipic acid.

SUMMARY OF THE INVENTION

The present invention is a process for the preparation of 3-pentenoic acid which comprises reacting in a solvent consisting essentially of at least one carboxylic acid selected from the group of aliphatic $C_2$-$C_{20}$ carboxylic acids, benzoic acid and alkyl-substituted benzoic acids wherein the total number of carbons in the alkyl group(s) is not more than 3: butadiene, carbon monoxide, and water with a rhodium catalyst and a promoter selected from the class consisting of bromide and iodide, at a temperature in the range of about 40° C. to about 200° C. and at a carbon monoxide partial pressure in the range of about 75 to about 3000 psig, wherein the concentration of rhodium is in the range of about 0.005% to about 0.50% by weight of the total weight of the reaction mixture, and the molar ratio of promoter to rhodium is between about 1:1 and about 20:1.

DETAILED DESCRIPTION OF THE INVENTION

In U.S. Pat. No. 4,622,423, Burke disclosed that improved yields of adipic acid can be obtained in the hydrocarboxylation of butadiene if the reaction is conducted in two steps. The process described in '423 gives high yields of the desired linear hydrocarboxylation product, 3-pentenoic acid, in the first step to adipic acid. However, the rate of formation of 3-pentenoic acid is quite low in the suitable solvents of the '423 process. In U.S. Pat. No. 4,788,334, Burke showed that the use of aromatic or aliphatic acids can dramatically increase the rate of hydrocarboxylation of linear olefinically unsaturated esters and linear terminally unsaturated alkenes. Although it was found that the highest reaction rates for the hydrocarboxylation of 1-hexene were obtained in "neat" acetic acid, linearity was substantially reduced compared to hydrocarboxylation reactions run in solvent mixtures containing methylene chloride.

This invention provides a process for the hydrocarboxylation of butadiene which gives both high reaction rates and high linear selectivity to 3-pentenoic acid. The invention is a process for the preparation of 3-pentenoic acid which comprises reacting in a solvent consisting essentially of at least one carboxylic acid selected from the group of aliphatic $C_2$-$C_{20}$ carboxylic acids and benzoic acid, and alkyl-substituted benzoic acid wherein the total number of carbon atoms in the alkyl group(s) is not more than 3: butadiene, carbon monoxide, and water with a rhodium catalyst and a promoter selected from the class consisting of bromide and iodide, at a temperature in the range of about 40° C. to about 200° C. and at a carbon monoxide partial pressure in the range of about 75 to about 3000 psig, wherein the concentration of rhodium is in the range of about 0.005% to about 0.50% by weight of the total weight of the reaction mixture, and the molar ratio of promoter to rhodium is between about 1:1 and about 20:1.

The process of this invention can be run either as a batch or as a continuous process.

The temperature of the reaction is in the range of about 40° C. to about 200° C.; 100° C.-180° C. is preferred and 130° C.-160° C. is most preferred. Below 40° C., the reaction becomes too slow to be commercially feasible, and above 200° C. the formation of undesirable products (e.g., butadiene polymers) leads to significant yield losses and reactor fouling.

Suitable total pressures are in the range 300-3000 psig, with 400-1200 psig being preferred. The partial pressure of carbon monoxide is usually maintained in the range 75-3000 psig, preferably 200-1000 psig.

The source of the reactants for the present process is not particularly critical. Commercially available grades of carbon monoxide (CO) and butadiene (BD) are satisfactory. The carbon monoxide can contain inert impurities such as carbon dioxide, methane, nitrogen, noble gases, and paraffinic hydrocarbons having from 1 to 4 carbon atoms. The carbon monoxide can also contain hydrogen. The hydrocarboxylation of butadiene to form 3-pentenoic acid requires at least a 1:1 molar ratio of CO:BD, however an excess of CO is generally used.

The amount of unreacted butadiene in the reaction mixture should be controlled such that its concentration is less than 20 wt. % of the solution. The concentration of butadiene can be controlled by continuous or stepwise addition of BD to the reaction.

Suitable solvents for this process are aliphatic $C_2$–$C_{20}$ monocarboxylic acids, aliphatic $C_4$–$C_{20}$ dicarboxylic acids, benzoic acid, alkyl-substituted benzoic acids, and mixtures thereof. The preferred solvents are aliphatic $C_2$–$C_6$ monocarboxylic acids, $C_4$–$C_7$ dicarboxylic acids, benzoic acid and mixtures thereof. The most preferred solvents are acetic, propionic, butyric, 2-methylbutyric, valeric, and caproic acids and mixtures thereof. Mixtures of monocarboxylic and dicarboxylic acids produced directly or indirectly in the hydrocarboxylation of butadiene can also be used in whole or in part as the solvent for this process. Such monocarboxylic and dicarboxylic acids include adipic, valeric, 2-methylglutaric, ethylsuccinic and methylbutyric acids.

It has been found that certain halocarbon solvents (e.g., methylene chloride) are unstable under the reaction conditions described by the process of this invention, especially at high temperatures. In the process of this invention, halocarbon solvents such as methylene chloride appear to hydrolyze, forming products which react with butadiene to lower the yield of the desired adipic acid. The use of halocarbon solvents is therefore to be avoided in the process of this invention.

Water, which is necessary for the hydrocarboxylation of butadiene, can be obtained from water added to the reaction mixture or from water formed under the reaction conditions (for example from the formation of esters or anhydrides). Although water is necessary for the hydrocarboxylation of butadiene, it should not be present in large excess. Preferably water is present in an amount of less than 15%, more preferably less than 10%, and most preferably less than 5%, based on the weight of the reaction mixture. (The weight of the reaction mixture includes the weight of the solvent(s), catalyst(s), promoter(s) and reactants.) The water may be present in the solution at the beginning of the reaction or it may be added continuously as consumed by the reaction to avoid undesirably high concentrations.

The rhodium catalyst can be provided from any source or by any material which will produce rhodium ions under hydrocarboxylation conditions. Among the materials which can be employed as the source of the rhodium catalyst are rhodium metal, rhodium salts, rhodium oxides, rhodium carbonyl compounds, organorhodium compounds, coordination compounds of rhodium, and mixtures thereof. Specific examples of such materials include, but are not limited to, rhodium-(III) chloride and its hydrates, $RhI_3$, $Rh(CO)_2I_3$, $Rh(CO)I_3$, rhodium(III) nitrate trihydrate, $Rh_4(CO)_{12}$, $Rh_6(CO)_{16}$, $Rh(acac)_3$, $Rh(CO)_2(acac)$, $Rh(C_2H_4)_2(acac)$, $Rh(C_2H_4)_2Cl]_2$, $[Rh(CO)_2Cl]_2$, $Rh(COD)(acac)$, $[Rh(COD)Cl]_2$, $RhCl(CO)(PPh_3)_2$, $Rh_2[O_2C(CH_2)_6CH_3]_4$ and $Rh_2(acetate)_4$, where acac is acetylacetonate and COD is 1,5-cyclooctadiene. Supported rhodium compounds, e.g. Rh/C and Rh/alumina, can also be used as a source of the rhodium catalyst. Rhodium compounds containing bidentate phosphine or nitrogen ligands should be avoided. Preferred sources of the rhodium catalyst include rhodium(I) compounds such as $[Rh(CO)_2Cl]_2$, $[Rh(COD)Cl]_2$, and $Rh(COD)(acac)$ and rhodium iodide compounds such as $RhI_3$ and $Rh(CO)_2I_3$.

Suitable concentrations of rhodium in the reaction medium are in the range of 0.005–0.50 % by weight of rhodium metal based on the weight of the reaction medium. Preferably, the concentration of rhodium is in the range of 0.01–0.20 wt. %, more preferably 0.02–0.10 wt. %. Rh concentrations below 0.20 wt. % are preferred to minimize the conversion of BD to unwanted by-products.

The rhodium catalyst, which can be preformed or formed in situ, must be promoted by bromide or iodide, preferably iodide, to achieve a satisfactory reaction rate. The promoter can be provided by HX (X=I, Br), $X_2$, MX (M=alkali metals), $M'X_2$ (M'=alkaline earth metals), transition metal bromides, transition metal iodides, including certain rhodium halides, or any organic halide which will provide bromide or iodide. Suitable sources of bromide or iodide include bromine, iodine, HI, HBr, organic bromide compounds, organic iodide compounds, and mixtures thereof. Preferred sources of iodide and bromide include HI, HBr, acetyl bromide, acetyl iodide, lower alkyl bromides ($C_1$–$C_{10}$) and lower alkyl iodides ($C_1$–$C_{10}$), such as methyl bromide, bromoethane, 1-bromobutane, 1,4-dibromobutane, 2-bromopropane, 1-bromopropane, bromoheptane, methyl iodide, iodoethane, 1-iodobutane, 1,4-di-iodobutane, 2-iodopropane, 1-iodopropane and iodoheptane. The promoter and rhodium can also be present in the same compound, e.g., as in $RhI_3$. The most preferred sources of promoters are HI, HBr and methyl iodide.

The molar ratio of promoter to rhodium is critical to obtaining the high rates and yields of this invention. Although high selectivities can be obtained even at low promoter-to-Rh ratios, the rate of formation of 3-pentenoic acid on a per Rh basis decreases significantly when the molar ratio of promoter-to-Rh is less than about 1. At the current high cost of rhodium ($20,000 per lb), it is, therefore, more economical to operate at a promoter-to-rhodium ratio greater than 1. Similarly, the molar ratio of promoter-to-Rh must be less than about 20 to obtain high selectivity to 3-pentenoic acid. Preferably, the molar ratio of promoter to rhodium is between about 1 and 15; more preferably between about 1 and about 8; most preferably between about 2 and about 6.

By keeping the promoter to rhodium ratio within these low and rather narrow limits, the dual and usually conflicting goals of high reaction rate and high linear selectivity for butadiene hydrocarboxylation in carboxylic acid solvents can be achieved. This result is quite surprising in view of the art since it has not previously been recognized that the promoter to rhodium ratio has any significant effect on product distribution. For example, it was recognized by Burke (U.S. Pat. No. 4,788,334) that the linearity of the hydrocarboxylation of 1-hexene decreased with increasing accelerator concentrations at I/Rh=10. But the influence of the I/Rh ratio on linearity was not examined. In U.S. Pat. No. 3,579,552, Craddock et al. reported the hydrocarboxylation of several olefin substrates in acetic acid using I/Rh ratios between 15 and 312, but were similarly silent on the influence of I/Rh on the product distribution. Moreover, the results obtained by Craddock et al. for the hydrocarboxylation of butadiene in acetic acid (Ex. 9, I/Rh=132) make the product distribution and selectivity of the present invention especially surprising: As shown in the Comparative Example (below), butadiene hydrocarboxylation under Craddock's conditions gives large amounts of reduced C5 acids, principally methylbutyric and valeric acids. Only trace amounts of 3-pentenoic acid, which is the dominant product in the process of the present invention, are formed.

As illustrated in the Examples below, the selectivity in the hydrocarboxylation of butadiene to 3-pentenoic acid is very high (up to 87%) as long as some butadiene is still present in the reaction mixture. When more than about 80–90% of the butadiene has been converted to products, the amount of 3-pentenoic acid recovered from the reaction slowly decreases as it is consumed in other reactions.

The following examples are presented to illustrate, but not to restrict the present invention. Parts and percentages are by weight and temperatures are in degrees Celsius unless otherwise noted.

EXAMPLES

EXAMPLE 1

This example illustrates the use of $RhCl_3.3H_2O$ and HI, where $I/Rh=1$.

Acetic acid (70 g.) containing 0.28 g of water and 0.164 g of 56% aq. HI was cold pressured to 100 psig with CO and heated to 150° C. in a 100 mL Hastelloy-C mechanically stirred autoclave. After reaching 150° C., a solution of 0.183 g of $RhCl_3.3H_2O$ in 1.3 g or water was injected with CO to bring the overall unit pressure to 400 psig. Butadiene (BD, 3.2 g) was injected immediately with enough additional CO to bring the final reactor pressure to 700 psig. Samples were withdrawn at 30, 60, 120, 180, and 240 min. Initial BD/Rh=85, initial I/Rh =1, initial water/BD=1.6. Butadiene half-life was 58 min. Material balance, butadiene-to-products recovered, is 72%, increasing to 81% if normalized to the fraction of mass recovered.

Samples were treated with $BF_3$/methanol to convert the carboxylic acid groups to the corresponding methyl esters by heating aliquots (0.1 g) of the reaction mixture for 1 h at 90° C. with 1 mL of 12% $BF_3$ methanol containing 0.003 g of o-dichlorobenzene as an internal standard. The derivatized samples were then cooled, quenched with 1 mL of water, and extracted with 2 mL of methylene chloride. The methylene chloride phase was analyzed using temperature-programmed elution on a capillary GC column. "%Selectivity" is the number of moles of product per 100 moles of BD charged.

| Time (min)        | 30  | 60  | 120 | 180 | 240 |
|-------------------|-----|-----|-----|-----|-----|
| % Selectivity to: |     |     |     |     |     |
| 3-pentenoic acid  | 47  | 71  | 87  | 81  | 79  |
| valeric acid      | 0   | 0   | 0.  | 0.4 | 0.7 |
| valerolactone     | 0.4 | 0.8 | 1.9 | 4.8 | 6.7 |
| ethylsuccinic acid| 0.1 | 0.2 | 0.2 | 0.6 | 0.9 |
| methylglutaric acid| 0.8| 1.2 | 1.7 | 4.5 | 6.2 |
| adipic acid       | 0.6 | 2.8 | 1.2 | 3.1 | 4.3 |
| 2-butanone        | 1.5 | 0.2 | 0.9 | 1.4 | 2.0 |
| BD dimers         | 0.5 | 0.8 | 0.8 | 0.2 | 0.3 |

Nearly 90% of the recovered products were pentenoic acids until essentially all butadiene had apparently reacted (as reflected in the marginal increase in recovered products after 120 min).

EXAMPLE 2

This example illustrates the use of a rhodium(I) compound, $[Rh(CO)_2Cl]_2$, and HI, where $I/Rh=3.1$.

Acetic acid (69 g) and $[Rh(CO)_2Cl]_2$ (0.14 g) were cold-pressured to 100 psi with CO and heated to 150° C. After this solution reached 150° C., 2.2 9 of water, 0.48 g of 56% aq. HI, and 2.1 g of acetic acid were injected with CO bringing the unit pressure to 400 psig. BD (3.0 g) was immediately introduced with CO to bring the final unit pressure to 700 psig. Samples were taken at 10, 20, 30, 40, and 120 min. Initial BD/Rh=82, initial I/Rh=3.1, initial water/BD=2.4. Butadiene was completely converted by the first sample. Material balance, butadiene-to-products recovered, is 82%, increasing to 88% if normalized to the fraction of mass recovered. Samples were analyzed as described in Example 1.

| Time (min)         | 10  | 20   | 30   | 40   | 120  |
|--------------------|-----|------|------|------|------|
| % Selectivity to:  |     |      |      |      |      |
| 3-pentenoic acid   | 79  | 67   | 59   | 49   | 9    |
| valeric acid       | 2.0 | 2.4  | 3.3  | 3.6  | 5.7  |
| methylbutyric acid | 0.8 | 1.0  | 1.5  | 1.6  | 2.7  |
| valerolactone      | 3.1 | 6.0  | 7.5  | 9.6  | 18.1 |
| ethylsuccinic acid | 1.1 | 1.9  | 2.4  | 3.2  | 6.0  |
| methylglutaric acid| 6.4 | 11.2 | 14.3 | 17.8 | 32.2 |
| adipic acid        | 4.4 | 8.0  | 10.7 | 13.4 | 25.6 |
| 2-butanone         | 2.7 | 2.6  | 2.2  | 1.7  | 0.6  |
| BD dimers          | 0.5 | 0    | <0.1 | <0.1 | <0.1 |

EXAMPLE 3

Example 2 was repeated with faster sampling.

The procedure described in Example 2 was substantially repeated, using faster sampling. Initial BD/Rh=80, initial I/Rh=3.0, initial water/BD=2.5. Butadiene was still essentially totally converted by the first sample. Material balance, butadiene-to-products recovered, was 84%, increasing to 90% if normalized to the fraction of mass recovered. Samples were analyzed as described in Example 1.

| Time (min)         | 1   | 4   | 7   | 10  | 60   |
|--------------------|-----|-----|-----|-----|------|
| % Selectivity to:  |     |     |     |     |      |
| 3-pentenoic acid   | 79  | 79  | 75  | 73  | 21   |
| valeric acid       | 0.8 | 1.4 | 1.7 | 2.1 | 3.9  |
| methylbutyric acid | 0.3 | 0.5 | 0.7 | 0.9 | 1.7  |
| valerolactone      | 1.7 | 3.5 | 4.3 | 4.4 | 14.9 |
| ethylsuccinic acid | 0.6 | 1.1 | 1.4 | 1.5 | 5.2  |
| methylglutaric acid| 3.3 | 6.2 | 7.8 | 8.9 | 28.7 |
| adipic acid        | 2.3 | 4.2 | 5.5 | 6.2 | 22.2 |
| 2-butanone         | 1.5 | 3.7 | 3.3 | 2.8 | 1.4  |
| BD dimers          | 1.3.| 0.4 | 0.2 | 0.2 | 0    |

EXAMPLE 4

This example illustrates the use of $[Rh(CO)_2Cl]_2$ and HI, where $I/Rh-1$.

The procedure described in Example 1 was repeated using $[Rh(CO_2C]_2$ (0.1 g) in place of $RhCl_3.3H_2O$. Initial BD/Rh=82, initial I/Rh=1.1, initial water/BD=2.3. Material balance, butadiene-to-products recovered, was 87%, increasing to 100% if normalized to the fraction of mass recovered. The halflife for BD disappearance was reduced to 25 min, but the selectivities are comparable to those reported for Example 1, in which the halflife was 58 min. Samples were analyzed as described in Example 1.

| Time (min)         | 10  | 20  | 30  | 40  | 120 |
|--------------------|-----|-----|-----|-----|-----|
| % Selectivity to:  |     |     |     |     |     |
| 3-pentenoic acid   | 26  | 40  | 50  | 59  | 84  |
| valeric acid       | 0   | 0   | 0.1 | 0.2 | 0.7 |
| methylbutyric acid | 0   | 0.6 | 0.7 | 1.0 | 0.3 |
| valerolactone      | 0   | 0.7 | 0.6 | 0.7 | 2.8 |
| ethylsuccinic acid | 0   | 0   | 0   | 0.2 | 0.7 |
| methylglutaric acid| 0.1 | 0.6 | 0.7 | 0.9 | 4.5 |
| adipic acid        | 0   | 0.8 | 0.7 | 0.1 | 3.0 |
| 2-butanone         | 2.2 | 2.1 | 2.6 | 2.7 | 3.2 |

| Time (min) | 10 | 20 | 30 | 40 | 120 |
|---|---|---|---|---|---|
| BD dimers | 0.8 | 1.2 | 0.6 | 1.1 | 0.8 |

EXAMPLE 5

This example illustrates the use of pre-reduced $RhI_3$: $RhI_3$ was pre-reduced by mixing 11.3 g $RhI_3$ and 1.3 g of $Rh_2(OAc)_4$ with enough acetic acid/water (65%/35%) to make a total of 100 g of solution, and then stirring the solution at 100° C. under 150 psi of CO for 3 h to produce a clear yellow-to-amber solution. Material balance, butadiene-to-products recovered, was 80%, increasing to 82% if normalized to the fraction of mass recovered. Samples were analyzed as described in Example 1.

| Time (min) | 3 | 6 | 9 | 15 | 60 |
|---|---|---|---|---|---|
| % Selectivity to: | | | | | |
| 3-pentenoic acid | 77 | 78 | 77 | 69 | 29 |
| valeric acid | 0.7 | 1.1 | 1.4 | 1.7 | 4.4 |
| methylbutyric acid | 0.5 | 0.5 | 0.6 | 0.7 | 2.3 |
| valerolactone | 2.5 | 5.3 | 5.1 | 6.9 | 13.9 |
| ethylsuccinic acid | 0.3 | 0.9 | 1.2 | 1.9 | 5.4 |
| methylglutaric acid | 1.9 | 5.2 | 6.5 | 10.1 | 27.3 |
| adipic acid | 1.3 | 3.6 | 4.3 | 6.3 | 16.7 |
| 2-butanone | 0.5 | 0.7 | 0.5 | 0.4 | 0.3 |
| BD dimers | 2.3 | 0.6 | 0.5 | 0.2 | 0.1 |

EXAMPLES 6–10

These examples illustrate the effect of I/Rh on product distribution.

A 100 cc autoclave was charged with 69 g of acetic acid and 0.14 g of $[Rh(CO)_2Cl]_2$. The unit was cold pressured to 100 psi with CO and heated to 140° C. while the reaction mixture was stirred. The unit was then brought to 400 psi with CO while introducing 3 g of acetic acid and the quantities of 57% aq HI and water shown in Table 1. Butadiene (3.5 g) was added via syringe pump and the unit brought to 700 psi with additional CO. The reaction was sampled at the indicated times, and the product mix analyzed by gas chromatography as described in Example 1. There was extensive plugging in Examples 8–10. Also, intermediate samples showed that the catalyst died rather rapidly in Examples 9 and 10, in which I/Rh=12 and 20, respectively. The results are summarized in Table 1.

TABLE 1

Effect of I/Rh on Product Distribution

| Ex. No. | Wt. H₂O (g) | Wt. 57% aq HI(g) | Wt % HI | I/Rh ratio | Time (min) | % Material Balance Yield | | | |
|---|---|---|---|---|---|---|---|---|---|
| | | | | | | PAs | VL | DBAs | (AA) |
| 6 | 1.20 | 0.48 | 0.6 | 3 | 10 | 92 | 1 | 3 | (1) |
| | | | | | 32 | 80 | 5 | 12 | (4) |
| 7 | 1.00 | 0.96 | 1.2 | 6 | 32 | 77 | 13 | 10 | (4) |
| 8 | 0.80 | 1.44 | 1.8 | 9 | 32 | 18 | 9 | 18 | (6) |
| 9 | 0.58 | 1.92 | 2.4 | 12 | 32 | 51 | 7 | <1 | (0.4) |
| 10 | 0.00 | 3.27 | 4.0 | 20 | 32 | 23 | 5 | <1 | (0) |

"DBAs" = Dibasic acids, i.e., adipic, ethylsuccinic and methylglutaric acids.

EXAMPLES 11–12

These examples, together with Example 6, illustrate the effect of water concentration.

A 100 cc autoclave was charged with 69 g of acetic acid and 0.14 g of $[Rh(CO)_2Cl]_2$ and the amount of water shown in Table 2. The unit was cold pressured to 100 psi with CO and heated to 140° C. while the reaction mixture was stirred. The unit was then brought to 400 psi with CO while introducing 3 g of acetic acid, 0.48 g of 57% aq HI and 1.2 g of water. Butadiene (3.5 g) was added via syringe pump and the unit brought to 700 psi with additional CO. The reaction was sampled at the indicated times, and the product mix analyzed by gas chromatography as described in Example 1. The results are summarized in Table 2.

TABLE 2

Effect of Water on Product Distribution

| Ex. No. | Wt. H₂O added (g) | Wt. % water | Water/ feed | I/Rh ratio | Time (min) | % Material Balance Yield | | | |
|---|---|---|---|---|---|---|---|---|---|
| | | | | | | PAs | VL | DBAs | (AA) |
| 6 | 0.0 | 1.8 | 1.2 | 3 | 10 | 92 | 1 | 3 | (1) |
| | | | | | 32 | 80 | 5 | 12 | (4) |
| 11 | 3.0 | 5.5 | 4.0 | 3 | 32 | 61 | 2 | 10 | (2) |
| 12 | 7.0 | 10.0 | 7.2 | 3 | 32 | 53 | 2 | 2 | (0) |

"DBAs" = Dibasic acids, i.e., adipic, ethylsuccinic and methylglutaric acids.

EXAMPLE 13

This example illustrates the use of $[Rh(COD)Cl]_2$ and HI at 140° C.

A 300 mL Hastelloy-C mechanically stirred autoclave was flushed with nitrogen and then with high purity CO. It was then charged with 150 mL of an acetic acid solution containing 0.37 g (1.5 mmole) $[Rh(COD)Cl]_2$ and 5.0 g o-dichlorobenzene (internal GC standard). The autoclave was closed and butadiene was injected with CO pressure from a charge cylinder containing 8.1 g (150 mmole) butadiene. The autoclave was pressured with CO to 400 psi and then heated to 140° C. The reaction was initiated by injecting into the autoclave a solution made by dissolving 1.0 g of 57% aq HI (4.5 mmole HI) in 2.7 g (150 mmole) water. The autoclave pressure was then immediately adjusted to 700 psi with CO. The pressure was maintained at 700 psi by feeding CO from a reservoir. The carbonylation rate was measured by monitoring the reservoir pressure drop.

Uptake of CO was extremely rapid (>50% of total over the first 15 min), after which the rate of uptake slowed.

The reaction was allowed to run for a total of 2 h, after which it was cooled to 20° C. The excess CO was vented and the product was discharged. The autoclave was washed first with 150 mL of methanol at 100° C. under autogenous pressure and then with 100 mL methanol at room temperature.

GC analysis of the reactor vapor phase showed that the butadiene concentration had decreased from 5.89% to 0.35% after 2 h (94% conversion). The half-life for BD disappearance was 11 min. This analysis also showed that the concentration of 1- and 2-butenes in the reactor gas phase after 2 h was 0.16% (about 4 % of the initial BD concentration) and that the concentration of $CO_2$ was 1.91%

The product and washes from the autoclave were combined, filtered and then the filtrate was diluted to 500 mL with methanol. A sample of this solution was esterified by heating it in a sealed vial at 90° C. for 14 h with p-toluenesulfonic acid and excess methanol. The methyl esters were analyzed by capillary GC as shown below:

| | |
|---|---|
| t-3-pentenoic acid | 17.94% |
| c-3-pentenoic acid | 5.87% |
| 2-pentenoic acid | 0.75% |
| 4-pentenoic acid | 0.48% |
| g-valerolactone | 7.99% |
| 2-methyl-3-butenoic acid | 0.79% |
| valeric acid | 1.75% |
| adipic acid | 10.35% |
| 2-methylglutaric acid | 12.17% |
| ethylsuccinic acid | 2.21% |

These compositions are reported as moles per 100 moles of BD charged, even though control experiments showed that 25-30% of the BD in the charging cylinder did not enter the reactor. No other products were detected in significant amounts, and no tars were formed.

This reaction was allowed to run for many half-lives, resulting in considerable conversion of the desired 3-pentenoic to other products. However, at least 74% of the products (the pentenoic acids, g-valerolactone, valeric acid, and adipic acid) represent the desired 3-pentenoic acid or its derivatives. An additional 24% of the acid-containing products could be derived from either an initial linear or nonlinear hydrocarboxylation of butadiene.

EXAMPLE 14

This example illustrates the use of HBr as a promoter.

The procedure described in Example 13 was repeated, except that the HI was replaced by an equivalent amount (4.5 mmole) of HBr (0.76 g, 46% aq HBr). The reaction was allowed to run for 5 h at 140° C. and 700 psi total pressure. The initial gas phase BD concentration was 7.63% and was 1.87% after 5 h (75.5% conversion). The corresponding concentrations of butenes was 0.028% and 0.25%. Work-up and GC analysis of the product showed only 25% recovered butadiene, 3.3% mixed butenes, and 12.1% t-and c-3-pentenoic acids. No other products were detected in significant amounts and no tars were formed. (As in Ex. 13, 25-30% of the BD in the charging cylinder did not enter the reactor.)

COMPARATIVE EXAMPLE

This example illustrates the use of a high promoter-to-Rh ratio (I/Rh=132), as disclosed in Example 9 of Craddock et al.

Acetic acid (51.8 g), water (1.8 g), $RhCl_3 \cdot 3H_2O$ (0.075 g), 57% aq HI (8.48 g) and butadiene (9.75 g) were cold pressured to 200 psig with CO, heated to 175° C., and then brought to 685 psig final pressure with CO. The unit was held at this condition for 24 h, cooled and vented. The final product mix was very complex, but the following material balance yields were observed:

| | |
|---|---|
| methylbutyric acid | 15% |
| valeric acid | 10 |
| BD polymers (solids) | 9 |
| BD dimers (in sol'n) | 2 |
| 2-iodobutane | 2 |
| butyl acetate | 2 |
| pentenoic acids | 0.3 |
| valerolactone | 0.2 |
| (lesser quantities of ethylbenzene, xylenes, many $C_9$ acids) | |

The saturated $C_5$ monoacids constitute 62% of the identified peaks.

I claim:

1. A process for the preparation of 3-pentenoic acid which comprises reacting in a solvent consisting essentially of at least one carboxylic acid selected from the group of aliphatic $C_2$–$C_{20}$ carboxylic acids, benzoic acid, and alkyl-substituted benzoic acid wherein the total number of carbon atoms in the alkyl group(s) is not more than 3: butadiene, carbon monoxide, and water with a rhodium catalyst and a promoter selected from the class consisting of bromide and iodide, at a temperature in the range of about 40° C. to about 200° C. and at a carbon monoxide partial pressure in the range of about 75 to about 3000 psig, wherein the concentration of rhodium is in the range of about 0.005% to about 0.50% by weight of the total weight of the reaction mixture, and the molar ratio of promoter to rhodium is between about 1:1 and about 20:1.

2. The process according to claim 1 wherein the solvent consists essentially of at least one carboxylic acid selected from the group consisting of aliphatic $C_2$–$C_{20}$ monocarboxylic acids, and aliphatic $C_4$–$C_{20}$ dicarboxylic acids.

3. The process according to claim 2 wherein the solvent consists essentially of at least one carboxylic acid selected from the group consisting of aliphatic $C_2$–$C_6$ monocarboxylic acids, and aliphatic $C_4$–$C_7$ dicarboxylic acids.

4. The process according to claim 3 wherein the solvent consists essentially of at least one carboxylic acid selected from the group consisting of acetic, propionic, butyric, 2-methylbutyric, valeric and caproic acids.

5. The process according to claim 4 wherein the solvent consists essentially of acetic acid.

6. The process according to claim 3 wherein the solvent consists essentially of at least one carboxylic acid selected from the group consisting of adipic, valeric, 2-methylglutaric, ethylsuccinic and methylbutyric acids.

7. The process according to claim 1 wherein the concentration of Rh is between about 0.01 wt. % and about 0.20 wt. %.

8. The process according to claim 7 wherein the partial pressure of carbon monoxide is between about 200 psig and about 1000 psig.

9. The process according to claim 8 wherein the temperature is between about 100° C. and about 180° C.

10. The process according to claim 9 wherein the molar ratio of promoter-to-Rh is between about 1:1 and about 15:1.

11. The process according to claim 10 wherein the promoter is iodide.

12. The process according to claim 11 wherein the source of the promoter is HI or $CH_3I$.

13. The process according to claim 11 wherein the molar ratio of iodide-to-Rh is between about 1:1 and about 8:1.

14. The process according to claim 13 wherein the concentration of Rh is between about 0.02 and about 0.10 wt. %.

15. The process according to claim 14 wherein the temperature is between about 130° C. and about 160° C.

16. The process according to claim 15 wherein the molar ratio of iodide-to-Rh is between about 2:1 and about 6:1.

17. The process according to claim 16 wherein the concentration of water is less than 15 wt. %.

18. The process according to claim 17 wherein the concentration of butadiene is less than about 20 wt. %.

19. The process according to claim 18 wherein the concentration of water is less than about 10 wt. %.

20. The process according to claim 19 wherein the concentration of water is less than about 5 wt. %.

* * * * *